United States Patent
Tibbetts

(10) Patent No.: US 7,961,323 B2
(45) Date of Patent: Jun. 14, 2011

(54) MICROARRAY IMAGING SYSTEM AND ASSOCIATED METHODOLOGY

(75) Inventor: Clark Tibbetts, Sperryville, VA (US)

(73) Assignee: Tessarae, LLC, Sterling, VA (US)

( * ) Notice: Subject to any disclaimer, the term of this patent is extended or adjusted under 35 U.S.C. 154(b) by 1055 days.

(21) Appl. No.: 11/684,484

(22) Filed: Mar. 9, 2007

(65) Prior Publication Data

US 2007/0263914 A1    Nov. 15, 2007

Related U.S. Application Data

(60) Provisional application No. 60/780,616, filed on Mar. 9, 2006.

(51) Int. Cl.
  *G01N 21/25* (2006.01)
(52) U.S. Cl. ........................................ 356/417
(58) Field of Classification Search .................. 356/300, 356/303, 310, 317; 382/129
  See application file for complete search history.

(56) References Cited

U.S. PATENT DOCUMENTS

| | | |
|---|---|---|
| 2001/0054701 A1 | 12/2001 | Nishioka et al. |
| 2003/0169357 A1 | 9/2003 | Kubo |
| 2005/0006595 A1 | 1/2005 | Goodwin et al. |
| 2005/0030535 A1 | 2/2005 | Rassman et al. |
| 2005/0030625 A1* | 2/2005 | Cattin-Liebl ................ 359/560 |
| 2005/0110998 A1 | 5/2005 | Lin et al. |
| 2005/0191756 A1* | 9/2005 | Corson et al. ................ 436/164 |
| 2005/0221351 A1 | 10/2005 | Ryu |
| 2005/0260741 A1 | 11/2005 | Albertson et al. |
| 2005/0269523 A1* | 12/2005 | MacAulay et al. ........ 250/458.1 |
| 2005/0282156 A1 | 12/2005 | Rava et al. |
| 2006/0176481 A1* | 8/2006 | Forest et al. .................. 356/344 |
| 2007/0166771 A1* | 7/2007 | Kapur et al. .................. 435/7.2 |

* cited by examiner

Primary Examiner — Tarifur Chowdhury
Assistant Examiner — Abdullahi Nur
(74) Attorney, Agent, or Firm — Oblon, Spivak, McClelland, Maier & Neustadt, L.L.P.

(57) ABSTRACT

An apparatus and method are provided for creating an image of a microarray. The apparatus includes at least one light source configured to direct light toward the microarray. The apparatus includes an excitation filter configured to filter the light into a first frequency band towards dichromatic mirror. The dichromatic mirror reflects light onto the microarray causing the microarray to emit electromagnetic energy. The apparatus includes emission filter configured to filter the electromagnetic energy within a second frequency band. The apparatus further includes an imaging unit having a charged coupled device (CCD), the CCD having an imaging surface masked by a pinhole blind such that when the pinhole blind receives electromagnetic energy from the emission filter, an image is created of the entire microarray.

11 Claims, 11 Drawing Sheets

MICROARRAY IMAGING SYSTEM AND ASSOCIATED METHODOLOGY

CROSS REFERENCE TO RELATED APPLICATIONS

This application claims benefit of the earlier filing date of U.S. Provisional Application No. 60/780,616, filed Mar. 9, 2006, entitled "Simple Imaging System for Applications of Microarrays at Points of Use," the entire contents of which are herein incorporated by reference.

BACKGROUND OF THE INVENTION

Analytical microarrays typically function as commercial analytical tools for research and other applications. Such tools study a wide variety of specific interactions and properties of molecular entities, most particularly nucleic acids, proteins, carbohydrates, lipids and a myriad of specifically or generically binding ligand molecules. Microarrays vary in overall size but are often on the order of 1 $cm^2$ to 1 $in^2$. The Microarray includes ordered and addressed positions, or cells, or features, each feature bearing physically attached, abundant copies of an identical probe entity. Rectangular arrays may range from as few as about 25 distinct features (as in 5×5) to as many as 2,500,000 distinct features (as in 1600× 1600), with feature dimensions (diameter or square edge) ranging from 1 mm to 1 μm.

Typically, microarrays are fabricated or manufactured by manual or robotic depositions of probe entities to specified feature sites, or alternatively, the probe entities may be synthesized de novo, in parallel at specific feature sites of the array, using photochemical lithographic processes. Novel extensions or modifications of probes may also be used to adapt probe entities, taking advantage of unique or generic chemical or biochemical properties of the intermediate probe constructs.

Once assembled, a microarray represents a multiplex platform for analysis of specific and non-specific interactions with simple or complex mixtures of molecular targets that are brought into physical contact with the array, typically in a medium of surface-solution interface. Target entities may be generically or specifically labeled, as with fluorescent tags or intermediate binding elements such as biotin, before or after the interaction of target mixtures with fixed-probe arrays. Alternatively, site-specific interactions across the array may be monitored by target- or ligand-induced changes in labels associated with probe entities on the fixed array surface.

In the specific context of fluorescent labels, optical imaging provides the path for quantitative estimation of the extent of target-probe interaction, feature by feature across the array. Multiple fluorescent labels offer the opportunity to assess relative extents of interactions among different target entities at the same probe sites.

A notable variation on the rectangular microarray format and rationale is the application of suspended microspheres. In this configuration, each sphere is uniquely labeled with one or more fluorescent labels, and offers unique probe entities for interaction analysis on the sphere surface. As an example, the Luminex Corporation of Austin, Tex. offers such a suspended microsphere system.

Suspended multiplex mixtures of microspheres may be segregated by probes interacting with specific target entities bearing affinity markers for secondary binding to treated surface. Additionally, probes may segregate paramagnetic beads. As an example, the Invitrogen Corporation of Carlsbad, Calif. offers paramagnetic beads under the brand name Dynabeads®. Differentiation of beads isolated from mixtures is based upon fluorescence signature of dye labels embedded in the beads, by scanning beads settled onto an arrayed or random surface, or by direct flow cytometry of individual beads in suspension.

Fluorescent microarray image data acquisition is typically performed using mechanically and optically elaborate instrumentation with precise mechanical stage transport control and confocal epifluorescence measurements, for pixel by pixel sampling across the microarray field. Most often one or more lasers may be used to provide sufficient excitation illumination during the brief dwell time for photodetector measurement of fluorescence signal(s) at each pixel site. These systems are quite costly, typically on the order of $22 K-$180 K.

Such scanning detector systems are available for single arrays, or automated serial loading of multiple arrays for analysis, or for high throughput mechanical positioning of arrays of arrays in familiar microtiter trays—up to 96 microarrays per tray.

Presently, a simplified and more economical configuration is desired, devoid of the aforementioned limitations.

BRIEF SUMMARY OF THE INVENTIONS

An exemplary embodiment of the present inventions is directed to an apparatus for creating an image of a microarray. The apparatus includes at least one light source configured to direct light toward the microarray having addressed probes with at least on label that is activated by the targets. The apparatus has an excitation filter configured to filter the light into a first frequency band and a dichromatic mirror configured to reflect the light in the first frequency band onto the microarray causing the microarray to emit electromagnetic energy from the labels activated by the target at a frequency range that transmits through the dichromatic mirror. The apparatus includes an emission filter configured to filter the electromagnetic energy within a second frequency band. The apparatus further includes an imaging unit including a charged coupled device (CCD), the CCD having an imaging surface masked by a pinhole blind such that when the pinhole blind receives electromagnetic energy from the emission filter, an image is created of the entire microarray.

Another exemplary embodiment of the present inventions is directed to a method for creating an image of a microarray. The method directs light toward the microarray having addressed probes with at least on label that is activated by targets and filters the light into a first frequency band. The light is reflected in the first frequency band onto the microarray causing the microarray to emit electromagnetic energy from the labels activated by the target at a frequency range that transmits through the dichromatic mirror. The method further filters the electromagnetic energy within a second frequency band and forms an image of the entire microarray on a CCD having an imaging surface masked by a pinhole blind.

It is to be understood that both the foregoing general description of the invention and the following detailed description are exemplary, but are not restrictive, of the invention.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTIONS

The present inventions provide inter alia, a standalone method and apparatus, formed of individual components or modules and the imaging system as a whole as a component of a turnkey system for enabling on-site, near real time microarray analysis. Furthermore, these components and systems may have applications beyond this application as will be recognized by those of skill in the art. Likewise, the design and operation of the components and systems invite further miniaturization and improvements in manufacture and application.

In an exemplary embodiment, the imaging system leverages a lensless epifluorescent imaging system and uses advanced image deconvolution methodologies. The resulting method and apparatus provides an image data acquisition system that is suited to on-site and near real time analysis of genomic microarrays. Applications are not limited to medical diagnostics—as those of skill in the art will recognize applications in surveillance and screening, risk assessment and longitudinal tracking. Veterinary, agricultural, environmental, and biodefense applications often require robust and mobile field capabilities well served by the advancements described herein. The system described below is readily applied across a broader scope of close-field fluorescence, luminescence and bright field reflectance imaging applications, the description of which is omitted here for the sake of brevity.

Whole Array Imaging

Figure 1:
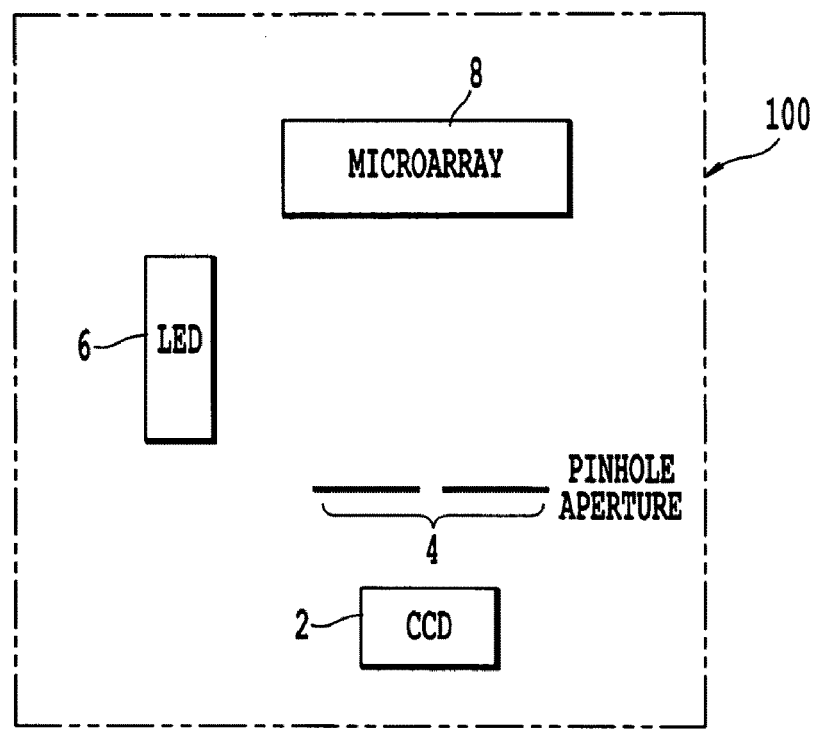
FIG. 1 is a high level block diagram of an exemplary embodiment of the imaging system in accordance with the inventions embraced by the specification.

FIG. 1 is a high level block diagram of the imaging system in accordance with the exemplary embodiment. The system, generally designated 100, includes a charge coupling device (CCD) 2, a pinhole aperture 4, a light emitting diode (LED) illumination array 6, and a microarray 8. In operation, the CCD 2 captures the image of the microarray 8 when a target on the microarray 8 is activated. For example, the LED illumination array 6 illuminates the microarry 8 activating a target on the microarray 8. Light emitted from an activated target on the microarray 8 passes through a pinhole aperture 4 onto the CCD 2.

An exemplary CCD 2 is a high-resolution charge coupled device (CCD) generating a simultaneous image of the microarray 8 in a single exposure. The CCD 2 is an image sensor consisting of an integrated circuit containing an array of linked, or coupled, light-sensitive capacitors serving as imaging pixels.

The exemplary CCD 2 oversamples the microarray 8 when capturing the image of the microarray 8. The CCD 2 oversamples the microarray when the number of imaging pixels of the CCD 2 exceeds the number distinct features of the microarray image. The number of imaging pixels per microarray features is referred to as the oversampling ratio. In an exemplary embodiment, the oversampling ratio ranges from 16 (4×4) to 100 (10×10) contiguous CCD 2 imaging pixels per microarray feature.

As an example, a microarray constructed as 100×100=10,000 distinct features in 1 $cm^2$ has features with approximately 100μ diameter (or square side). The image of such a microarray cast upon a 1 $cm^2$ CCD area with 500×500=250,000 imaging wells (pixels) provides an acceptable 25:1 oversampling ratio of CCD pixels per microarray feature. CCDs with such closely packed 20 μm pixels are commonly used today in consumer, professional and scientific cameras and imaging devices. A 1 $in^2$ CCD with about 3 million 15μ pixels would provide almost 300:1 oversampling of example 10,000 feature array, or 25:1 sampling of a 1 $cm^2$ array with about 100,000 features of 6 μm diameter (or square side).

The wide range of possible data oversampling offers opportunities to optimize data acquisition at different magnifications of the microarray image projected onto the CCD imaging device.

The digital oversampling rationale enables the data acquisition and analysis system to tolerate minor misalignments of the rectangular grids of features and pixels that define the microarray and CCD imaging array, respectively. The model provides sufficient data density to enable image processing techniques such as rotational matrix transformations to effect virtual alignment. Thus, the ease of oversampling enables raw image data processing to replace the precise mechanical positioning and orientation controls of conventional microarray scanning systems.

In the exemplary embodiment, a digital camera with a CCD's sensor is used for imaging a microarray. A discussion of digital cameras and CCD's suitable for imaging are found in HanVision Product Sheet (2004) HVDUO-10M digital color camera with Foveon X3® CMOS color image sensor; and Optronics Product Sheet—QuantiFIRE Advanced Scientific Grade [cooled] CCD Imaging for Microscopy, the entire contents of which are herein incorporated by reference.

Lensless Imaging—

Microarray scanning instruments in use today employ confocal microscope optics to focus the excitation (laser) light at the plane of the local area to be imaged on the array and to recover the emitted fluorescence light from the same small sampled spot. This implies mechanical as well as optical complexity in scanning traverses across the x-y plane of the array and in the perpendicular z-axis to ensure focus of the optical pathway on the plane of the array. In the exemplary embodiment, a minute pinhole aperture 4, as illustrated in FIG. 1, is used in place of precision mechanical transport controls and elaborate microscope optics.

The image resolution is inversely proportion to the dimension of the pinhole aperture 4. For example, the image resolution increases when the diameter of the pinhole aperture 4 decreases because the light entering the aperture is bent at a sharper angle. In the exemplary embodiment, pinholes are readily manufactured using lasers to perforate thin foils, with sizes on the order of one to several hundred μm. The lower limit of this range is consistent with the dimensions and imaging specifications disclosed above. Aside from physical and mechanical simplicity, the pinhole aperture approach offers the advantage of extraordinary depth of field—small variations in physical distance from the array surface, through the aperture to the imaging CCD will not affect the focal quality of the image.

Minimizing aperture size has two effects. First, the smaller aperture size requires increase in the exposure time, inversely proportional to the area of the aperture, in order to access sufficient light to produce the quantitative image of the array on the CCD. Second, the pinhole aperture diffracts the light passing through the aperture causing blurring patterns in the resulting image.

The blurring effects of diffraction are corrected in the raw digital CCD image using any desired deconvolution techniques for image processing. Deconvolution is the process of removing blurring effects from images. In an exemplary embodiment, deconvolution is achieved by multiplying the Fourier transform of the raw digital CCD image with the Fourier transform of the point spread function (PSF), and taking the inverse Fourier transform of that product. The PSF is a modeled function (empirical or theoretical) describing the spread of a point light source on the microarray plane through the aperture to the CCD imaging plane. The deconvolution method is illustrated in the equations below.

Let $f(x)$ represent the Fourier transform of signal x while $f^{-1}(\omega)$ represent the inverse Fourier transform of signal $\omega$. R is the received convoluted image on the CCD imaging plane. Y is a signal representing the PSF. Thus, $f(R)$ is the Fourier transform of the received image, while $f(Y)$ is the Fourier transform of the PSF. The Fourier transform product of the received image and the PSF is $$f(R) \cdot f(Y) \quad (1)$$

Let I represent the deblurred image. The deblurred image (i.e., deconvoluted image) is the image inverse Fourier transform of the Fourier transform product (1)

$$I = f^{-1}(f(R) \cdot f(Y)) \quad (2)$$

Figure 2:
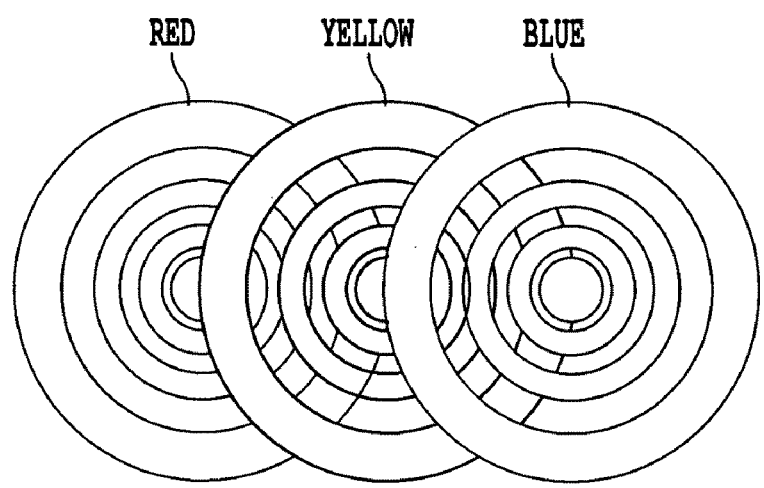
FIG. 2 is an image of a point spread function (PSF)

The empirical models of the PSF are readily obtained by imaging commercially available fluorescently stained microspheres on glass cover slips at the plane of microarray to be imaged. FIG. 2 illustrates the effect of light diffracted through a pinhole aperture on a CCD imaging plane. FIG. 2 shows the result of a point source of light passing through a pinhole aperture onto an imaging plane. Thus, FIG. 2 illustrates an empirical PSF. Ideally, one point of light should appear on the imaging plane. However, since the pinhole aperture diffracts light, concentric rings appear on the imaging plane. The diameter of the concentric rings depends on the wavelength of light, the size of the pinhole, and the focal length of pinhole to imaging plane. Taking the Fourier transform of image illustrated in FIG. 2 results in the Fourier transform of the PSF (i.e., $f(Y)$).

An exemplary embodiment uses the PS-Speck™ Microscope Point Source Kit with 0.175μ spheres with Green (505/515) and Orange (540/560) dye labels (excitation nm/emission nm) as fluorescent point sources for determining the empirical PSF. An alternative embodiment uses the InSpeck—Microscopy Intensity Calibration Kits, Green and Orange microspheres, 2.5 and 6.0μ, with relative fluorescence of 100%, 30%, 10%, 3%, 1% and 0.3% per sphere, as fluorescent point sources for determining the empirical PSF.

Software implementing algorithms are known to those skilled in the art to extract or predict the point spread functions for a particular imaging system and use these for image processing deconvolution.

High Power LED Illumination—

Conventional high performance confocal epifluorescence scanning systems for microarray image data acquisition use one or more lasers to illuminate the microarray for excitation and mapping of probe or target fluorophore labels. The high intensity of the laser beam provides sufficient illuminate during the brief transit period of the scanner in serial passage from one imaged pixel to the next.

An example of such confocal microarray scanning instrument is the aQuire system manufactured by the Genetix Corporation in Hampshire, UK. This system operates with up to three different lasers for illumination of familiar fluorophores used in nucleic acid analysis: 532 nm/575 nm filter (Cy3, Cy3.5, Alexa Fluors 532, 546, 555, 568, TAMRA); 639 nm/695 nm filter (Cy5, Cy5.5, Alexa Fluors 633, 647, 660, 680, BODIPY); 488 nm/535 nm filter (GFP, FITC, Alexa Fluors 488, 500, 514, Cy2 and Phycoerythrin). This confocal system can scan microarrays at 5 micron pixel resolution in about 1 minute per cm².

An exemplary embodiments of the present inventions uses the lower cost and longer service life of effective high power light emitting diodes (LED) 6, as illustrated in FIG. 1, to illuminate the entire array surface for the period of imaging exposure of the array to the CCD imager. Modem LED devices have been used for quantitative fluorescence analysis of labeled nucleic acids and proteins in methods such as real-time polymerase chain reaction (RTPCR). LED devices provide the advantages of longer lifetime, lower energy requirements, smaller size, simpler electronics and fewer operating hazards compared to laser systems. LED devices are available with emission wavelengths suited to the range of fluorescent label options in typical use with microarrays.

Figure 3:
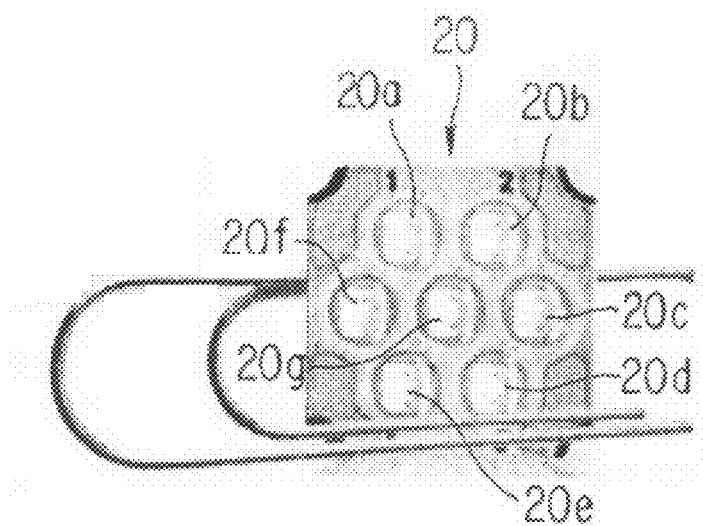
FIG. 3 is an image of an LED array in accordance with FIG. 1.

As an example, any desired high power LED may be used such as the high-power LEDs produced by the Lamina Ceramics Corporation in New Jersey. FIG. 3 shows an IC chip 20 having a hexagonal array of seven clusters (20a, 20b, 20c, 20d, 20e, 20f, 20g), each of which is a hexagonal array of six individual LED elements. Each LED element is embedded in a ceramic substrate that facilitates direct dissipation of heat from the LED.

Two examples of the B-2000 series of Lamina LED arrays produced by Lamina Ceramics are suitable as they provide intense, narrow bandwidth emission around 470 nm (blue) and 530 nm (green) wavelengths. These wavelengths are favorable for elicitation of fluorescence from fluorophores commonly used in the analysis of nucleic acids and proteins, particularly with respect to microarray applications, RT-PCR and other molecular biochemistry methodologies. Table 1 illustrates the specifications for particular LED arrays.

TABLE 1

| Series | Illumination Color | Wavelength Range | Power Rating | Luminous Flux |
|---|---|---|---|---|
| BL-22B1-0140 | Blue | 470 ± 5 nm | 4.5 W | 28 lumens |
| BL-22C1-0141 | Green | 525 ± 10 nm | 4.3 W | 78 lumens |
| BL-21E0-0131 | Amber | 589 ± 7 nm | 13.7 W | 290 lumens |
| BL-21A0-0121 | Red | 618 ± 5 nm | 13.6 W | 270 lumens |

Corbett Robotics of Australia manufactures a real time PCR instrument (the RotorGene-3000) that employs multiple LEDs with excitation wavelengths of 470 nm, 530 nm, 585 nm, and 625 nm (note correspondence to the Lamina LEDs, above) for multiplex fluorescence measurements using commonly used dye labels for nucleic acids, including Sybr-Green I, Fam, Tet, Joe, Vic, Max, Rox, Tamra, Cy3, Cy5, Cy5.5, Texas Red.

The performance of LED devices can be improved by (1) the dissipation of heat generated by the LED, and (2) uniformity of the distribution of light intensity across the array to be imaged. In an exemplary embodiment, LED design mount arrays of small LED elements (less than 1 mm$^2$) within a ceramic substrate that facilitates the transfer of heat from the devices to the conductive surface of an attached heatsink.

The dispersion of light from each of the LED elements in such arrays provide an increasingly simple Lambertian distribution at increasing distances from the light source.

Figure 4:
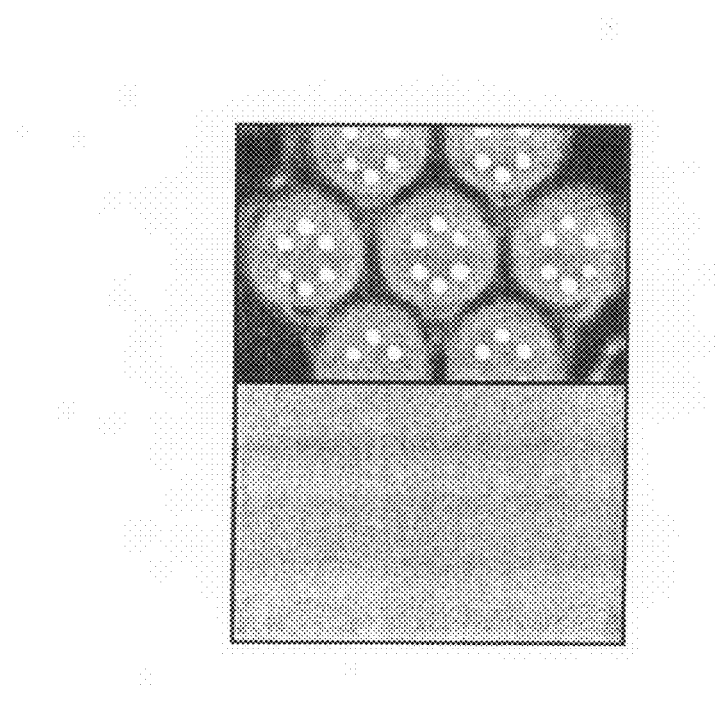
FIG. 4 is an image of the array of FIG. 3 illuminated LED in the upper pane and diffusion of light in the lower pane.

The placement of a holographic diffuser between the LED array and the illuminated microarray provides more nearly uniform illumination intensity across the array. FIG. 4 illustrates a Lamina Blue LED array. The upper pane of FIG. 4 shows direct imaging of a Lamina Blue LED array (Nikon D70) through a 260μ pinhole aperture. The pane below images the same LED array in the same configuration, with an intervening 40° circular holographic diffuser element (Edmond Industrial Optics, New Jersey) between the LED array and pinhole aperture. The lower pane illustrates that the holographic diffuser uniformly diffuses the illumination from the LED array. Thus, the individual LED's are not visible.

The exemplary embodiment is capable of handling the worst-case representation of illumination of an array, when the light dispersion design from each of the LED cavities is much broader than the aperture focused image of the LED source itself.

The same CCD imaging system for mapping fluorescence on the microarray can be configured to measure reflected incident light from the array surface, and support a computational correction of the CCD fluorescence images for variation in excitation light levels as a function of distance from the central point of the illumination field.

Figure 5:
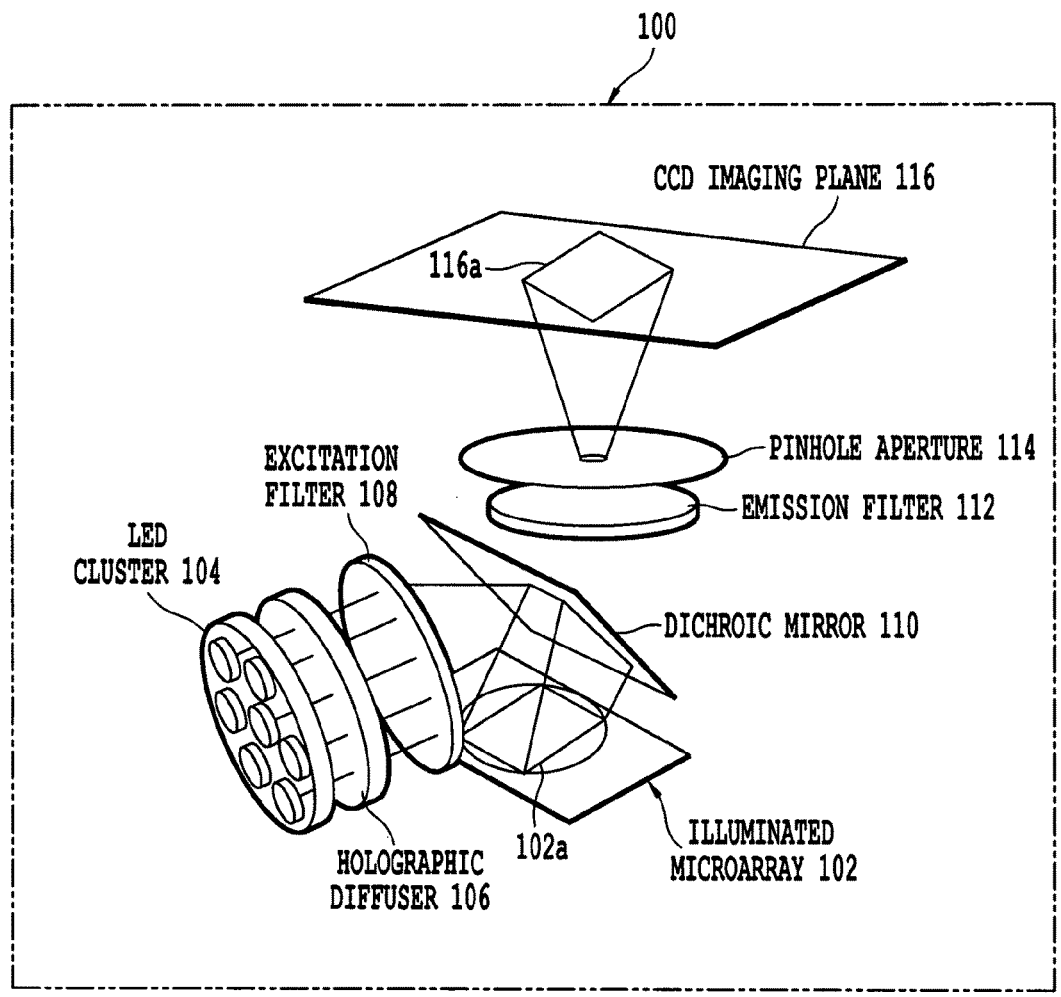
FIG. 5 is an expanded view of the imaging system of FIG. 1.

An exemplary embodiment of the complete imaging system 100 is illustrated in FIG. 5. As an example, shown in FIG. 5, a typical CCD camera having a CCD imaging plane 116 and detector 116*a* is used as the imaging device, with a pinhole aperture in a surface on the camera (in lieu of a mounted lens system). As an example, the typical distance from aperture to CCD plane 116 is about 50 mm, inviting a comparable working distance to contain the optical pathway from the microarray to the aperture.

According to exemplary embodiment of the present inventions, the physical distance between the array plane 102 and the CCD plane 116 from the intermediate pinhole aperture in the surface 114 is kept the same in order to contain the entire image of the microarray 102 within the physical dimensions of the CCD imaging plane 116. Some variation from equal distances can be advantaged to provide effective magnification or reduction of the array's image on the CCD plane. As discussed above, an advantage of the pinhole aperture is that its focal quality is independent of the working distance from the image source to the aperture.

The LED illumination array 104 illuminates the microarray 102 through a holographic diffuser 106 and excitation filter 108. As disclosed above, the holographic diffuser 106 increases the uniformity of the illumination intensity of the electromagnetic radiation emitted from LED illumination array. As an example, the working range of 1 to 2 inches is conveniently consistent with the dimensions of optical filter sets mounted in approximately 1 in$^3$ cubes for epifluorescence microscopes. Such filter cubes provide an excitation bandpass filter 108 on one face of the cube for entry of the illumination light field (from the LED array 104 in this invention). The excitation filter 108 allows illumination light at a desired wavelength pass through to the dichroic mirror 110 and microarry 102. The incident beam is reflected internally towards a perpendicular, open face of the cube by a dichroic mirror 110 mounted internally at a 45 degree angle with respect to the incident beam.

As shown in FIG. 5, the plane of the microarray 102 is placed in alignment with and proximity to the open cube face receiving the reflected incident light from the LED illuminator 104. Fluorescent targets 102*a* localized on the microarray surface 102 are treated as point light sources with the emission wavelength(s) characteristic of the particular fluorophore(s). Fluorescence in the opposite direction of the illumination beam (back into the cube) engages the same dichroic mirror 110, which in this case is transparent for fluorescence wavelengths longer than the excitation light. As the fluorescent light leaves the cube it passes through an emission bandpass filter 112 at the cube face opposite the microarray 102. In this example or prototype, the pinhole aperture in the surface 114 of the imaging system is placed in immediate proximity of the emission filter 112.

Figure 6:
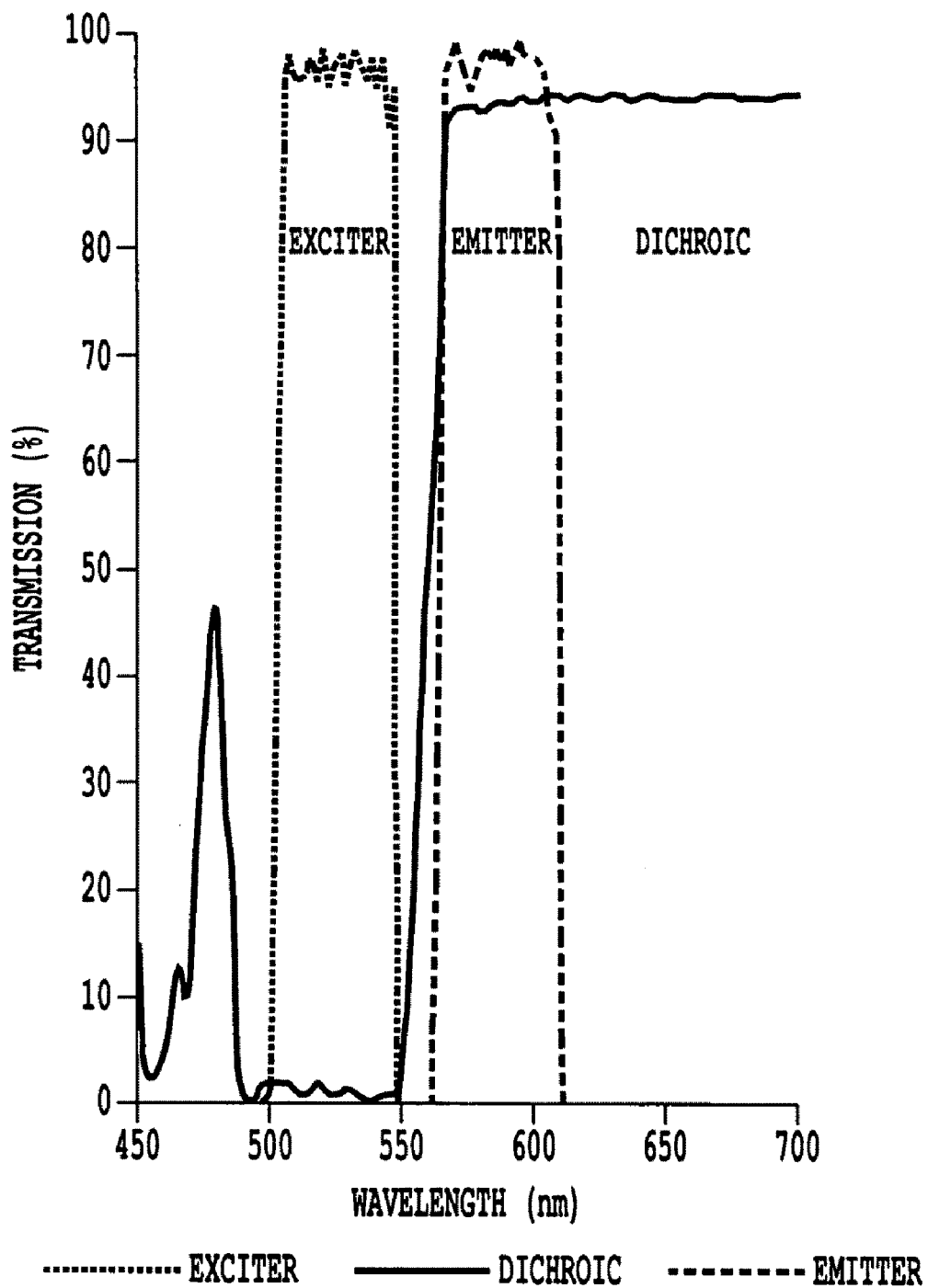
FIG. 6 is a graph of filter characteristics of an optical filter.
Figure 7:
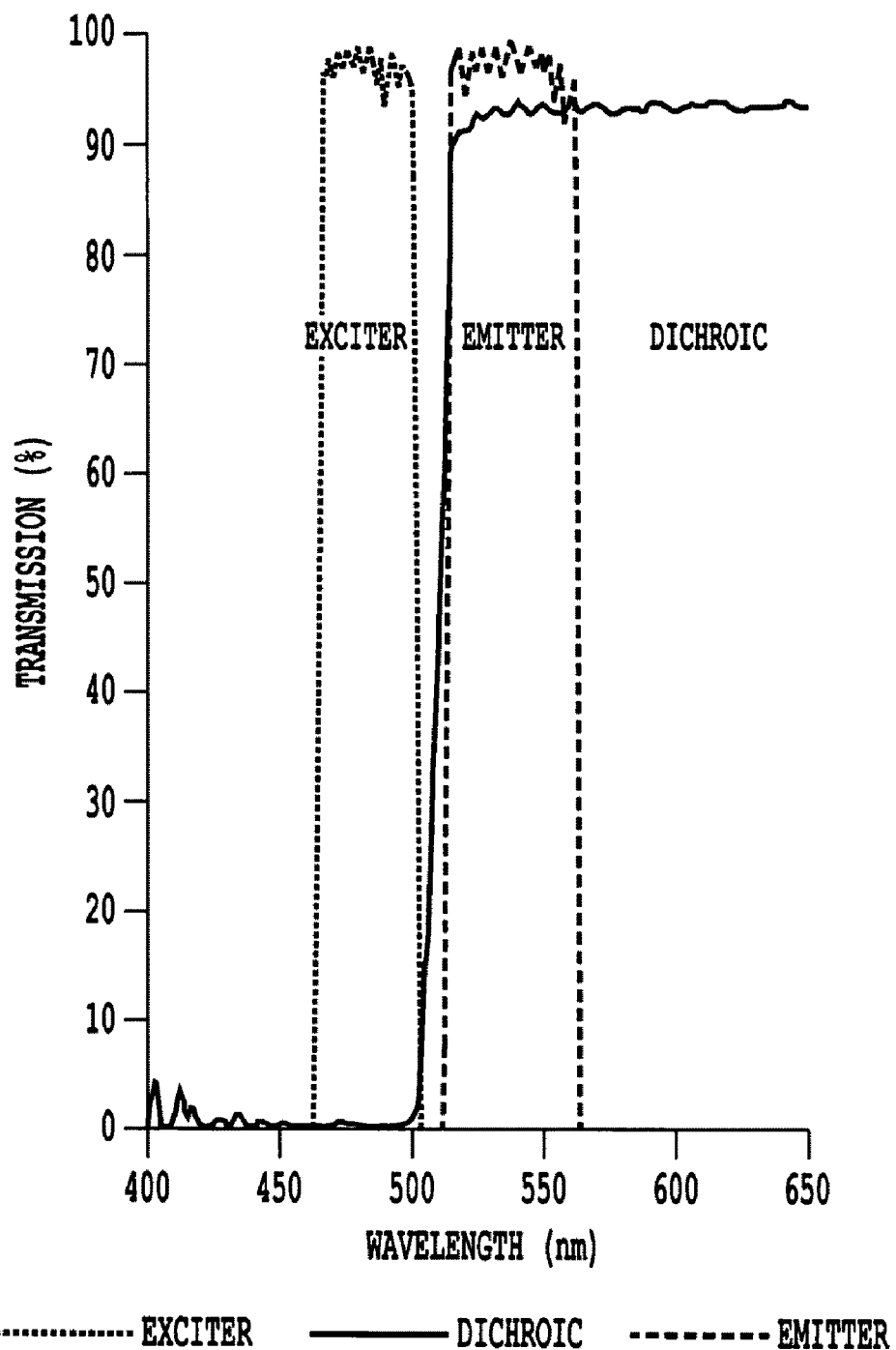
FIG. 7 is a graph of filter characteristics of an optical filter.

FIGS. 6 and 7 are graphs illustrating filter characteristics of two epifluorescence filters used in an exemplary embodiment of the present inventions. According to an exemplary embodiment of the present inventions, two products of the Semrock Corporation in New York—The FITC and TRITC filter sets can be used be used with the Lamina Blue (470 nm) (FIG. 6) and Green (525 nm) (FIG. 7) LED illumination arrays, respectively. Table 2 illustrates the characteristics of the filter sets.

TABLE 2

|  | Excitation | Dichroic | Emission |
|---|---|---|---|
| FITC Set (470 nm) | 460 nm-500 nm | 506 nm | 515 nm-555 nm |
| TRITC Set (525 nm) | 475 nm-545 nm | 555 nm | 560 nm-580 nm |

In another exemplary embodiment of the present inventions, the detector model includes serial imaging of the same microarray using different filter cubes and LED illuminators, to take advantage of multiple fluorophore labels on target mixtures interacting with the same microarray. Judicious selection of excitation and emission filters and dichroic mirror(s) for use with color imaging CCD arrays can also support simultaneous analysis of more than one fluorophore label.

If the microarray, as is typical, is fabricated on the surface of a transparent glass slide, or preferably a thin glass coverslip, then the array may be backed by a reflective mirror surface. This would provide a second pass of the incident beam through the fluorescent targets on the array surface, doubling the effective illumination of and presumably the fluorescent signal from the targets. There may be a perceived advantage also from the back reflection of fluorescence signal that might otherwise escape detection. However this latter signal is likely to degrade the quality of the fluorescent image at the CCD plane, due to refractive and angular diversity from point sources on the array surface. The practicality of this notionally four-fold signal enhancement approach remains to be determined. It is possible that practical advantage may be realized by application of additional deconvolution image processing steps or additional optical filtering components in the epifluorescence pathway.

Shutterless Exposure Control—

One design consideration is to minimize mechanical complexity (moving parts). An exemplary embodiment uses a digital camera for prototype imaging. In an alternative embodiment, a high resolution CCD imaging array is employed, which offers features of higher numbers of imaging pixels, and Peltier cooling to lower dark current and background of the CCD elements. In such an instance there are perceived advantages over use of a digital camera, particularly an SLR type of camera. If the CCD is optically contained, it is only exposed to low intensities of fluorescent light from the filter cube, and then only if a fluorescent microarray is under incident beam illumination. Since exposures through a pinhole aperture are anticipated to be of significant duration (seconds to minutes), a virtual electronic shutter (non-mechanical) may be employed. Instead of the mechanical flip of the SLR internal mirror, electronic signal to the CCD may flush the array of residual or background charge accumulations and effectively reinitiate photon collection (virtual shutter, no moving parts).

Coded Aperture Arrays—

As noted above, the fields of astronomy, microscopy and tomographic imaging have employed deconvolution image processing to clarify blurring from resolution-liming diffraction through small apertures. Some of these systems are not amenable to optical refraction for imaging, including x-ray telescopy or closer field imaging using single photon emission computed tomography (SPECT). Methodologies for these applications have developed to employ coded aperture arrays, with favorable results for both imaging resolution and reduction of exposure time.

Figure 8:
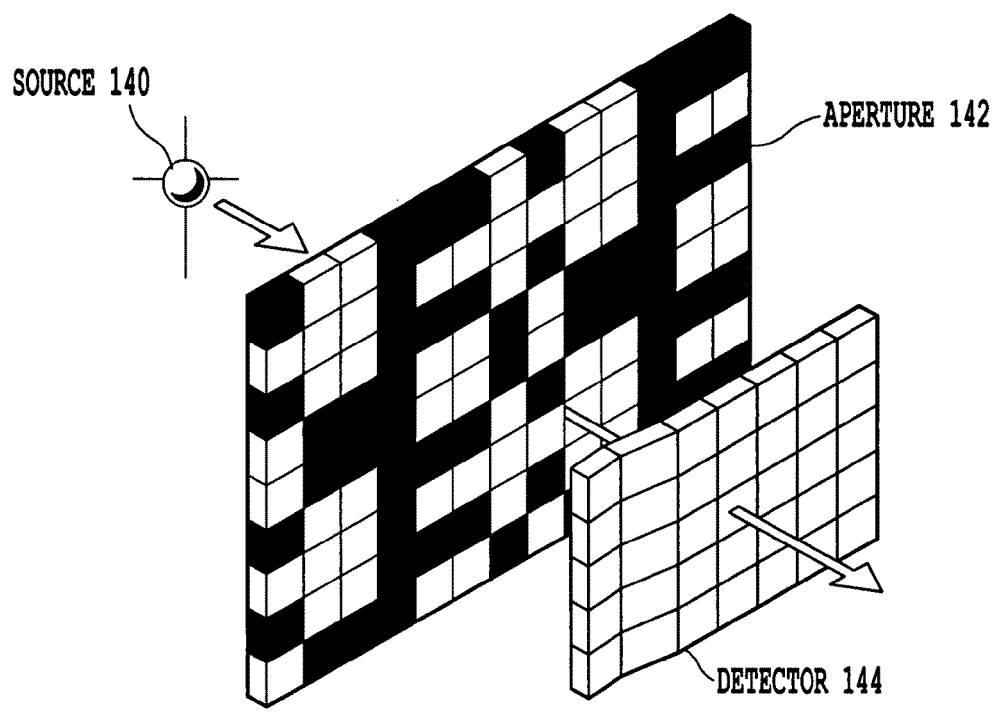
FIG. 8 is a schematic of a coded aperture array.

FIG. 8 illustrates an exemplary embodiment of a coded aperture array. The concept in FIG. 8 is that an array of pinhole apertures—random or pseudorandom, as a (modified) uniformly redundant array ((M)URA) layout—convolves or superimposes the image source as viewed through each of the apertures. A source light 8, such as an activated target in a microarray, passes through a coded aperture array 142 to a detector 144. The detector 144 is any desired imaging device such as a CCD.

The resulting image on the detector 144 is the convoluted image passing through the coded aperture array. The resulting image is blurred because the detector receives the light from multiple pinholes. Any desired image deconvolution techniques can be used to deblurr the resulting image. For example, let f(R) represent the Fourier transform of the convoluted image after passing through the coded aperture array, while M represents the inverse mask of the coded aperture array and f(M) represents the Fourier transform of the inverse mask. If I equals the deconvoluted image, then $$I = f^{-1}(f(R) \cdot f(M)) \text{tm (3)}$$

As illustrated in the equation above, an image cannot be deconvoluted (i.e. deblurred) without knowledge of the particular inverse mask of the coded aperture array. Thus, the inverse mask of the coded aperture array serves as an instantaneous optical encryption key for encrypting an image.

In an exemplary embodiment, the coded aperture array is designed to be an inverse of itself. The methods for creating a coded aperture array that is the inverse of itself and deblurring an image are described in Gottesman, S R and Fenimore, E E (1989) New family of binary arrays for coded aperture imaging. Appl Optics 28, 4344-4352; and Vanier (1973) Improvements in coded aperture thermal neutron imaging BNL-71468-2003-CP, the contents of which for all above noted references are herein incorporated by reference. A discussion of coded aperture arrays is also found in Fenimore, E E (1978) Predicted performance of uniformly redundant arrays. Appl Optics 17, 3562-3570; Fenimore, E E (1980) Coded aperture imaging: the modulation transfer function for uniformly redundant arrays. Appl Optics 19, 2465-2471; Fenimore, E E and Cannon, T M (1978) Coded aperture imaging with uniformly redundant arrays. Appl Optics 17, 337-347. (also note U.S. Pat. No. 4,209,780, same title and inventors); Accorsi, R (2001) Design of near field coded aperture cameras for high-resolution medical and industrial gamma-ray imaging. Doctoral dissertation, Massachusetts Institute of Technology, Cambridge, Mass.; and Accorsi, R, Gasparini, F and Lanza, R C (2001) A coded aperture for high resolution nuclear medicine planar imaging with a conventional Anger camera: experimental results. IEEE Trans Nuc Science 48, 2411-2417, the entire contents of which for all above noted references are herein incorporated by reference.

The Fourier transform-based convolution with the inverse of the coded aperture array mask leads to image reconstruction at resolution approaching the limit dimension of the coded aperture array's individual pinhole elements. Additionally, the exposure time for the (raw) image is reduced in proportion to the number of apertures in the mask.

Figure 9:
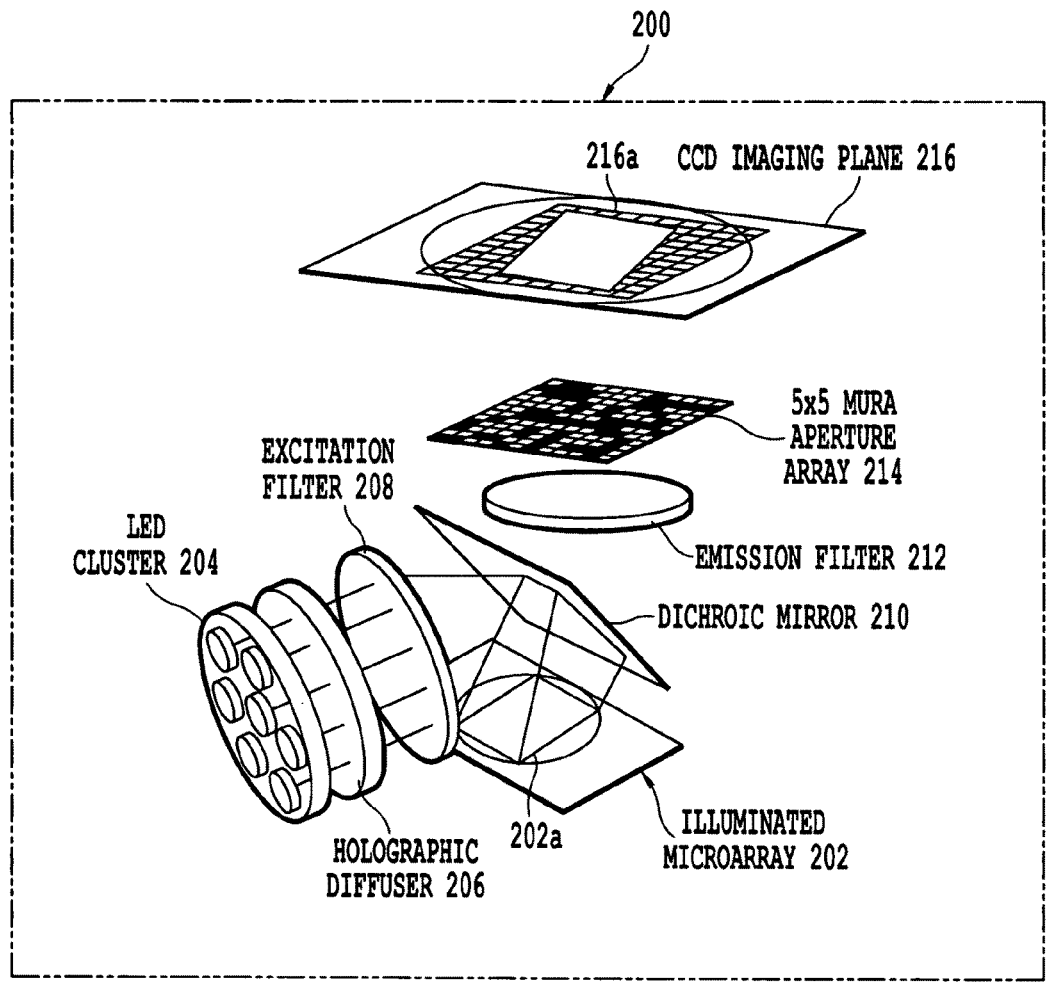
FIG. 9 is an expanded view of a further exemplary embodiment of the imaging system.

FIG. 9 illustrates another embodiment of an imaging system 200. The imaging system 200 includes a microarray 202 (with targets 202a), an LED illumination array 204, a holographic diffuser 206, and excitation filter 208, a dichroic mirror 210, and emission filter 212, and a CCD imaging plane 216 with a detector 216a. The functionalities of these components are similar to those described for the counterpart components described in FIG. 5. The imaging system 200 uses a coded aperture array 214 in place of the pinhole aperture 114 of FIG. 5.

The exemplary coded aperture array is a (M)URA of 211× 211 elements (open or closed) which offers nearly 50% open space and 22,000 times the light gathering power of a single element aperture.

Within the scope of this invention, the (M)URA or other designs of coded aperture arrays are fabricated for the intended application by means of high resolution black and white or color film reduction, as positive and or negative images of printed coded aperture arrays. This approach transcends the resolution limits of common digital printers in use today (about 25 g at 1400 dpi) to the finer resolution of familiar microfilm/microfiche substrates (1 to 5μ).

The application of microfilm as a substrate for generation of the coded is aperture arrays for this invention has similarities to a low-cost methodology for manufacture of photolithographic masks in MEMS manufacture. A description of MEMS is provided in Dotson, N A, Kim, P T, and Mason, A (2004) Low cost MEMS processing techniques. Proceedings of the 2004 ASEE/NCS Spring Conference, April (2004), the entire contents of which are herein incorporated by reference.

Furthermore, the use of color transparency film to generate the aperture masks provides opportunity in the domain of this invention for primary or secondary integration of optical (emission) filtering through the otherwise transparent open space of the aperture arrays.

This is envisioned as an economically viable and quality-assured pathway for production of these components for the subject invention as well as for other applications. It is also noted that the photolithographic masks used in the manufacture of particular microarrays are intrinsically of similar scale and complexity to the coded aperture array designs envisioned within the scope of this invention.

Translation of Raw Image Data to Decision Quality Information—

According to an exemplary embodiment of the present inventions, any desired CPU processor is connected to the CCD through any desired interface. The CPU processor has a memory device that stores the PSF empirical models and the inverse masks for coded aperture arrays. The CPU runs software or firmware for performing Fourier transforms, or any other desired algorithm, on any image captured by a CCD, the PSF empirical model, or inverse mask of a coded aperture array.

Likewise, those skilled in the art will recognize that any number of data processor may be employed such as programmable logic ASICS, a person computer, etc. An exemplary embodiment uses a digital signal processor (DSP) chip, implemented in the imaging system, for computing Fourier transforms, or any other desired algorithm, on any image captured by a CCD, the PSF empirical model, or inverse mask of a coded aperture array.

MURA Apertures—Preparation of Body Cap—

Figure 10:
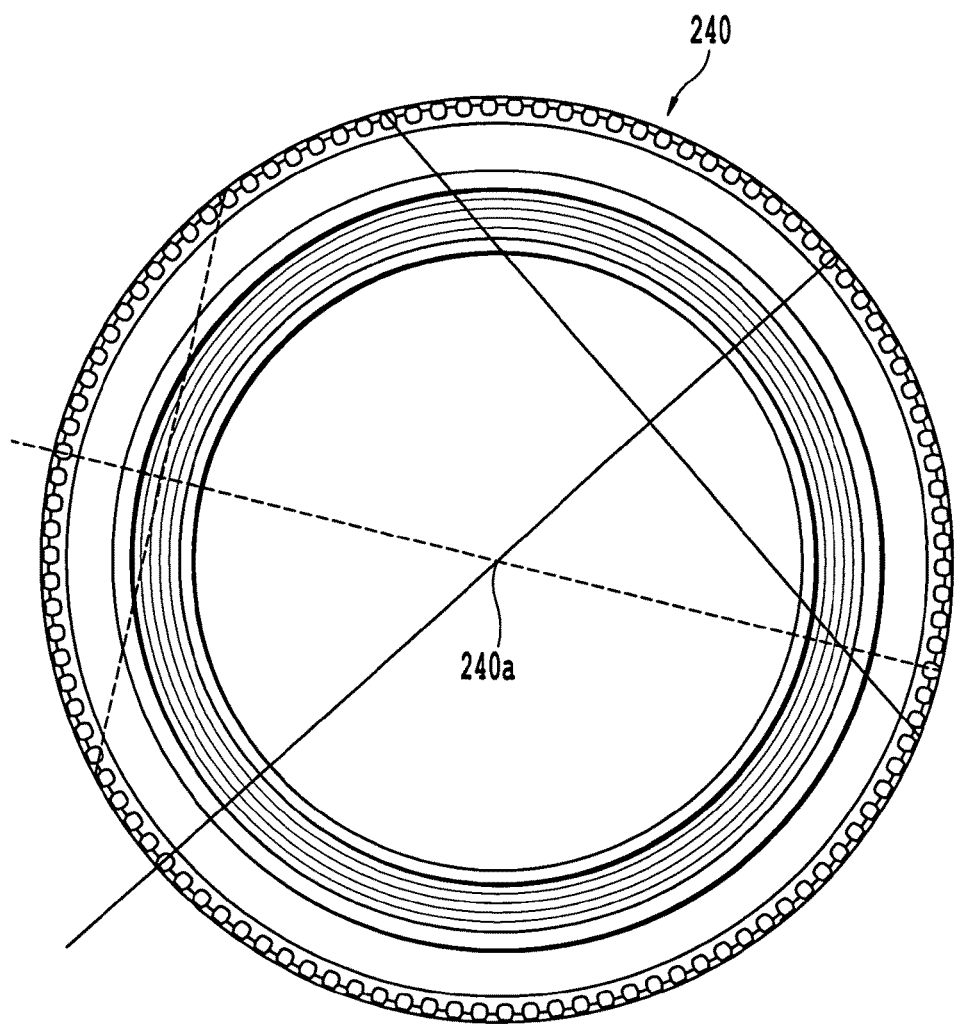
FIG. 10 is an image of a MURA aperture body cap.

As seen in FIG. 10, the front-plane of a standard black plastic body cap 240 was photographed. Digital image in Microsoft PowerPoint was enlarged, and a superimposed circle drawn to same diameter as the cap image. On the printed copy the geometric center of the circle was determined by intersection of two secants. A sharp steel punch is used to pilot the center for drilling an opening in the cap. A pinhole aperture is indicated by 240a. The cap is clamped to a wooden working surface and Dremel handtool, on low speed setting to prevent melting, is used to drill through the cap and enlarge the center hole incrementally from $1/16$ inch n $1/32$ inch increments. Final diameter selected to be just larger than diagonal of MURA element to be mounted. The front edges of opening are beveled using a conical stone or a $1/8$" piloted router bit with the Dremel handtool. Those skilled in the art will recognize that a standard camera body cap is not necessary, but used for a convenient description In another exemplary embodiment, the CCD device is masked by any desired surface having a pinhole aperture or coded aperture array, such as element 112 illustrated in FIG. 5 and element 212 illustrated in FIG. 6, respectively. Any surface having a pinhole aperture is referred to as a pinhole blind.

An exemplary embodiment uses A Mathematica (v5.2) program to construct and represent square MURA aperture arrays as digital images, following the explicit algorithmic description provided by Gottesman and Fenimore (1987) (cited above). A derivative image is constructed by black-white inversion and this image is centered within a white rectangle of dimensions 4 inches by 6 inches. The size of the square MURA in the center of the large rectangle is typically adjusted to represent each square aperture element of the array at 0.01 inch, 0.02 inch or 0.03 inch. When the composite rectangle and centered MURA image are photographed onto black/white negative film (see below), the approximately four-fold reduction of the rectangle's dimensions results in aperture element sizes on the film of 60μ, 120μ and 240μ, respectively.

Figure 11:
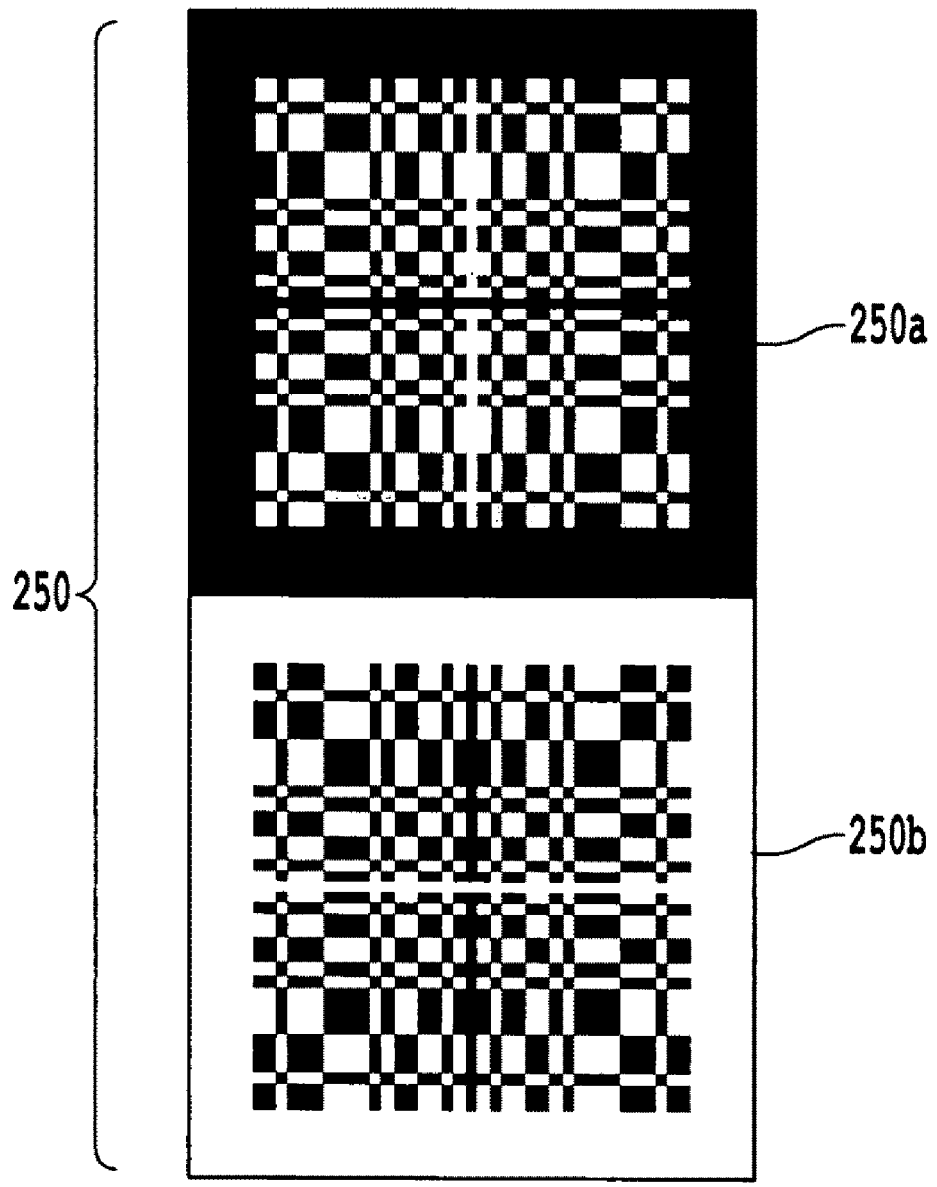
FIG. 11 is an image of a MURA positive array and a MURA negative array.

FIG. 11 illustrates a 37×37 element MURA positive array 250. The array includes a black background 250a and a corresponding negative array 250b having a white background. The negative image squares are sized to reduce to approximately 2.22, 4.44 and 8.88 mm sides, respectively. Diagonals of these square MURA images are thus approximately 3.14, 6.28 and 12.56 mm, respectively. These film negative images are then centered and mounted onto body caps with opening diameters of approximately $1/8$ inch, $1/4$ inch and $1/2$ inch, respectively.

Film Images of MURA Aperture Arrays—

Black/white images of the inverse MURA images are photographed (Nikon N80 camera) using a 60 mm Nikkor MICRO lens, with slow Ilford Delta 100 (ISO 100) 35 mm black and white negative film. The printed MURA inverse images were illuminated on a copy stand with four 5200 K photoflood lamps approximately 40 cm from the camera, and exposure speed settings at lens opening f8 are bracketed about the gray card metered speed of $1/120$th sec. Film was developed manually by black and white D71 process, with extended agitation to enhance contrast. Best results, as black opacity and white transparency are typically with exposures two to three times greater than the gray card metering—ie about $1/60^{th}$ sec at f8. Longer exposures increase opacity of black, but also result in increasing gray tone and loss of transparency of the white apertures.

Figure 12:
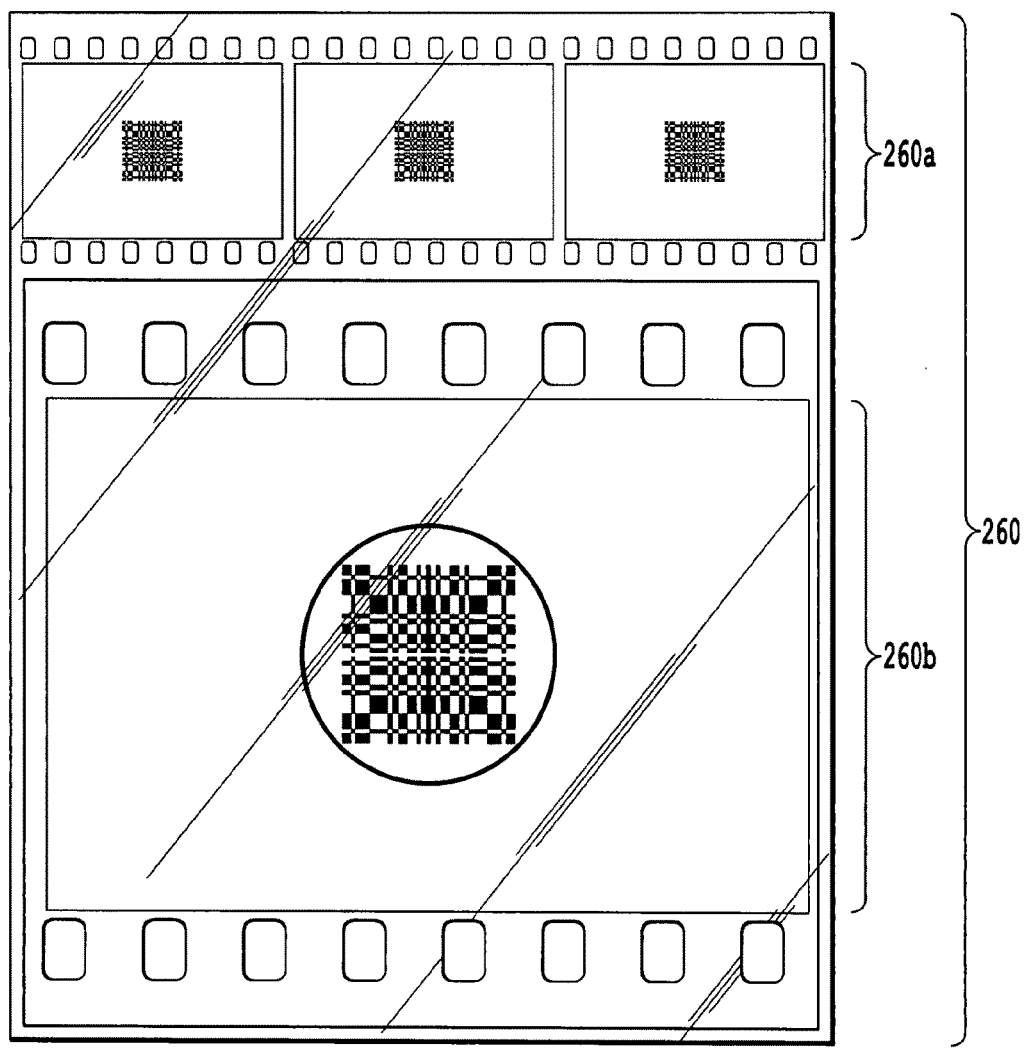
FIG. 12 illustrates black/white images of inverse MURA images.

FIG. 12 shows images of negatives scanned at 9600 dpi on HP officejet 5500v. The upper pane 260a shows bracketed exposures at $1/180^{th}$, $1/120^{th}$ and $1/90^{th}$ sec respectively. The gray card-metered exposure at $1/120^{th}$ sec is enlarged in the lower pane 260b to show detail. The circle represents the ½ inch opening in a Nikon body against which the MURA image is mounted.

The selected negative images of the MURA aperture arrays are trimmed at corners of the slide to fit as centered within the 37.5 mm diameter inner plane circle on the back of the Nikon BF-1A body cap. A 40 mm mounting disc is cut from black polystyrene sheet (Evergreen Scale Models, Woodinville, Va.; sheets 0.25 to 0.5 mm thick) from which a center hole is cut to match the centered opening in the body cap. The trimmed film negative is centered onto the body cap and covered then with the polystyrene disc, which is in turn fixed with small drops of plastic adhesive about its circumference.

In an alternative embodiment, the coded aperture array designed through the Mathematica program is implemented in any desired Computer Automated Design (CAD) program. Using the design implemented in the CAD program, the coded aperture array is etched onto a photolithographic mask. The photolithographic mask is then placed on the body cap of a camera. In an exemplary embodiment, the photoresist mask is a photoresist wafer having an area 1 cm². The coded aperture array is etched in a 3 mm² area in the center of the photoresist wafer with pinholes having a 100 micron diameter.

Figure 13:
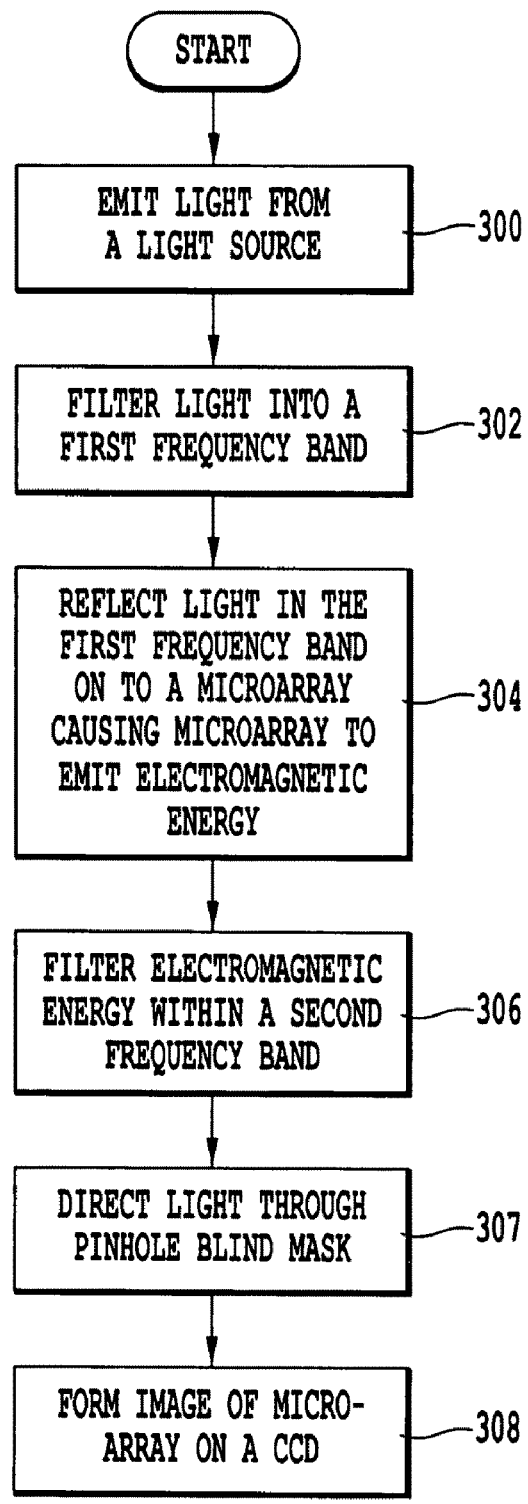
FIG. 13 is a flowchart of an exemplary method for creating an image of a microarray.

FIG. 13 is a flow chart illustrating an exemplary method for creating an image of a microarray. Step 300 emits light from a light source. Step 302 filters the emitted light into a first frequency band. Step 304 reflects light in the first frequency band onto a microarray causing the microarray to emit electromagnetic energy. Step 306 filters the electromagnetic energy within a second frequency band. Step 307 directs light through a pinhole blind mask. In an alternative embodiment, Step 307 directs light through a surface having a coded aperture array. Step 308 forms an image of the microarray on a CCD.

Any processes descriptions or blocks in flow charts should be understood as representing modules, segments, portions of code which include one or more executable instructions for implementing specific logical functions or steps in the process, and alternate implementations are included within the scope of the exemplary embodiment of the present invention in which functions may be executed out of order from that shown or discussed, including substantially concurrently or in reverse order, depending upon the functionality involved, as would be understood by those skilled in the art.

Obviously, readily discernible modifications and variations of the present invention are possible in light of the above teachings. It is therefore to be understood that within the scope of the appended claims, the invention may be practiced otherwise than as specifically described herein. For example, while described in terms of both software and hardware components interactively cooperating, it is contemplated that the system described herein may be practiced entirely in software. The software may be embodied in a carrier such as magnetic or optical disk, or a radio frequency or audio frequency carrier wave.

Thus, the foregoing discussion discloses and describes merely exemplary embodiment of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, define, in part, the scope of the foregoing claim terminology such that no inventive subject matter is dedicated to the public.

What is claimed is:

1. An apparatus for creating an image of a microarray, comprising:
    at least one light source configured to direct light toward the microarray having addressed probes with at least one label that is activated by targets;
    an excitation filter configured to filter the light into a first frequency band;
    a dichromatic mirror aligned with the microarray, the dichromatic mirror configured to reflect the light in the first frequency band onto the microarray causing the microarray to emit electromagnetic energy from the labels activated by the target at a frequency range that transmits through the dichromatic mirror;
    an emission filter configured to filter the electromagnetic energy within a second frequency band; and
    an imaging unit aligned with the microarray and dichromatic mirror, the imaging unit including a charged coupled device (CCD), the CCD having an imaging surface masked by a surface having a coded aperture array such that when the coded aperture array receives electromagnetic energy from the emission filter, an image is created of the entire microarray, wherein the coded aperture array is a modified uniformly redundant array (MURA).

2. The apparatus according to claim 1, wherein the enclosure further comprises:
    a data processor configured to receive the image of the entire microarray and perform image deconvolution by multiplying a Fourier transform of the image of the entire microarray with a Fourier transform of a inverse of the coded aperture array.

3. The apparatus according to claim 1, wherein a dimension of the MURA is at least 211×211 elements.

4. The apparatus according to claim 1, wherein the coded aperture array is configured to contain the inverse of itself.

5. The apparatus according to claim 1, further comprising:
    a holographic diffuser located between the at least one light source and the excitation filter; and
    the holographic diffuser configured to increase uniformity of a illumination intensity of the light emitted from the at least one light source.

6. The apparatus of claim 1, wherein a first distance between the CCD imaging surface and the coded aperture array is equal to a second distance between the microarray plane and the coded aperture array when the image of the microarray is created.

7. The apparatus according to claim 1, wherein the CCD is further configured to receive an electronic signal whereby the CCD is flushed of charge accumulations.

8. The apparatus according to claim 1, wherein the CCD further includes a number of imaging wells higher than a number of features in the microarray.

9. The apparatus according to claim 8, wherein a ratio of the number of imaging wells of the CCD to the number of features of the microarray is at least 25:1.

10. A method for creating an image of a microarray, comprising:
    directing light toward the microarray having addressed probes with at least one label that is activated by targets;
    filtering the light into a first frequency band;
    reflecting, by a dichromatic mirror aligned with the microarray, the light in the first frequency band onto the microarray causing the microarray to emit electromagnetic energy from the labels activated by the target at a frequency range that transmits through the dichromatic mirror;
    filtering the electromagnetic energy within a second frequency band; and
    forming an image of the entire microarray on a charged coupled device (CCD) aligned with the microarray and the dichromatic mirror, the CCD having an imaging surface masked by a surface having a coded aperture array that is a modified uniformly redundant array (MURA).

11. A method for optical encryption, comprising:
    reflecting, by a dichromatic mirror, light filtered into a first frequency band onto an object, the dichromatic mirror aligned with the object;
    receiving light from the object through a surface masked by a coded aperture array that is a modified uniformly redundant array (MURA); and
    forming an image of the object on a charged coupled device (CCD), aligned with the object and the dichromatic mirror, the CCD having an imaging surface, the coded aperture array configured to encrypt the image on the imaging surface of the CCD.

* * * * *